United States Patent
Butera et al.

[11] Patent Number: 5,225,566
[45] Date of Patent: Jul. 6, 1993

[54] INDAZOLANONYL DERIVATIVE OF BENZOPYRAN

[75] Inventors: John A. Butera, Kendall Park; Schuyler A. Antane, Plainsboro, both of N.J.

[73] Assignee: American Home Products Corporation, New York, N.Y.

[21] Appl. No.: 951,525

[22] Filed: Sep. 25, 1992

Related U.S. Application Data

[63] Continuation-in-part of Ser. No. 880,450, May 8, 1992, Pat. No. 5,179,118.

[51] Int. Cl.$^5$ .................................. C07D 405/04
[52] U.S. Cl. ........................................ 548/361.5
[58] Field of Search ............................ 548/361.5

[56] References Cited

FOREIGN PATENT DOCUMENTS 284174 9/1988 European Pat. Off. .

*Primary Examiner*—Robert W. Ramsuer
*Attorney, Agent, or Firm*—Richard K. Jackson

[57] ABSTRACT

The compounds of the formula:

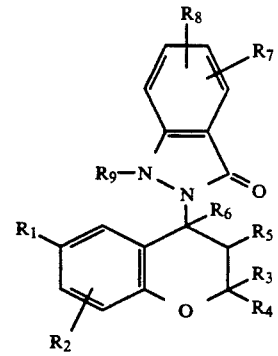

wherein $R_1$ is $C_{1-6}$ perfluoroalkoxy, $C_{1-6}$ perfluoroalkyl, $C_{1-6}$ alkyl, $C_{1-6}$ alkoxy, hydroxyl, $C_{2-6}$ alkoxycarbonyl, nitro, cyano, halogeno, $C_{1-6}$ alkylsulfonamido, $C_{1-6}$ perfluoroalkylsulfonamido, amino, $C_{2-6}$ alkanoylamino, $C_{2-6}$ perfluoroalkanoylamino, $C_{1-12}$ mono- or di-alkylamino, $C_{1-6}$ alkylsulfonyl, $C_{6-12}$ arylsulfonyl, carboxyl, or $C_{2-12}$ mono- or di-alkylcarbamoyl; $R_2$ is hydrogen, $C_{1-6}$ perfluoroalkoxy, $C_{1-6}$ perfluoroalkyl, $C_{1-6}$ alkyl, $C_{1-6}$ alkoxy, hydroxyl, $C_{2-6}$ alkoxycarbonyl, nitro, cyano, halogeno, $C_{1-6}$ alkylsulfonamido, $C_{1-6}$ perfluoroalkylsulfonamido, amino, $C_{2-6}$ alkanoylamino, $C_{2-6}$ perfluoroalkanoylamino, $C_{1-12}$ mono- or di-alkylamino, $C_{1-6}$ alkylsulfonyl, $C_{6-12}$ arylsulfonyl, carboxyl, or $C_{2-12}$ mono- or dialkylcarbamoyl; $R_3$ and $R_4$, independent from each other, are $C_{1-6}$ alkyl; either $R_5$ is hydrogen, hydroxyl, $C_{2-6}$ alkanoyloxy, $C_{7-12}$ aroyloxy, carbamoyloxy, formyloxy, $C_{2-6}$ alkoxycarbonyloxy, $C_{2-12}$ mono- or di-alkylcarbamoyloxy, and $R_6$ is hydrogen, or $R_5$ and $R_6$ together are a bond; $R_7$ and $R_8$, independent from each other, are selected from the following: $C_{1-6}$ perfluoroalkoxy, $C_{1-6}$ perfluoroalkyl, $C_{1-6}$ alkyl, $C_{1-6}$ alkoxy, hydroxyl, $C_{2-6}$ alkoxycarbonyl, nitro, cyano, halogeno, $C_{1-6}$ alkylsulfonamido, $C_{1-6}$ perfluoroalkylsulfonamido, amino, $C_{1-6}$ alkanoylamino, $C_{2-6}$ perfluoroalkanoylamino, $C_{1-12}$ mono- or di-alkylamino, $C_{1-6}$ alkylsulfonyl, $C_{6-12}$ arylsulfonyl, carboxyl, $C_{2-12}$ mono- or di-alkylcarbamoyl, or hydrogen; and $R_9$ is hydrogen, $C_{1-6}$ alkyl, $C_{2-6}$ alkylcarbonyl or $C_{1-6}$ alkylsulfonyl; or a pharmaceutically acceptable salt thereof are useful as smooth muscle relaxants, as antihypertensives and K channel activators.

1 Claim, No Drawings

INDAZOLANONYL DERIVATIVE OF BENZOPYRAN

RELATED APPLICATIONS

This application is a continuation-in-part of U.S. patent application Ser. No. 07/880,450, filed May 8, 1992, now U.S. Pat. No. 5,179,118.

BACKGROUND OF THE INVENTION

The present invention relates to novel benzopyrans having pharmacological activity, to a process for preparing them, to pharmaceutical compositions containing them, and to their use as smooth muscle relaxants in the treatment of hypertension and urinary incontinence via potassium channel modulation.

Recent reviews of potassium channel modulators are by: Longman et al., *Medicinal Research Reviews*, 1992, 12, 73; Robertson et al., *J. Med. Chem.* 1990, 33, 1529; Weston et al., TiPS 1990, 11, 417; and Evans et al., *Ann. Rep. Med. Chem.* 1991, 26, 73. Ashwood et al. disclose classes of chromans that are described as having blood pressure lowering activity in U.S. Pat. No. 4,616,021 and European Patent Publication 158,923. Quagliato et al. disclose classes of chromans that are described as having blood pressure lowering activity in U.S. Pat. Nos. 4,925,839 and 4,983,612. In addition, Soll et al. disclose a related class of chromans in U.S. Pat. No. 4,908,378. Yamanaka et al. disclose a series of hydrazido and hydrazino substituted chromans as having extremely long acting vasodilatory effects in EP-339,562-A2. Bruneau et al. disclose the synthesis of classes of substituted indazoles in European Patent Application 284,174 A1, although these compounds are described as inhibitors of the enzyme 5-lipoxygenase and thus useful in the area of inflammation.

DESCRIPTION OF THE INVENTION

Accordingly, the present invention discloses compounds represented by the formula (I):

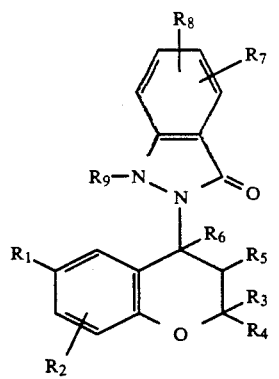

wherein:

$R_1$ is $C_{1-6}$ perfluoroalkoxy, $C_{1-6}$ perfluoroalkyl, $C_{1-6}$ alkyl, $C_{1-6}$ alkoxy, hydroxyl, $C_{2-6}$ alkoxycarbonyl, nitro, cyano, halogeno, $C_{1-6}$ alkylsulfonamido, $C_{1-6}$ perfluoroalkylsulfonamido, amino, $C_{2-6}$ alkanoylamino, $C_{2-6}$ perfluoroalkanoylamino, $C_{1-12}$ mono- or di-alkylamino, $C_{1-6}$ alkylsulfonyl, $C_{6-12}$ arylsulfonyl, carboxyl, or $C_{2-12}$ mono- or di-alkylcarbamoyl;

$R_2$ is hydrogen, $C_{1-6}$ perfluoroalkoxy, $C_{1-6}$ perfluoroalkyl, $C_{1-6}$ alkyl, $C_{1-6}$ alkoxy, hydroxyl, $C_{2-6}$ alkoxycarbonyl, nitro, cyano, halogeno, $C_{1-6}$ alkylsulfonamido, $C_{1-6}$ perfluoroalkylsulfonamido, amino, $C_{2-6}$ alkanoylamino, $C_{2-6}$ perfluoroalkanoylamino, $C_{1-12}$ mono- or di-alkylamino, $C_{1-6}$ alkylsulfonyl, $C_{6-12}$ arylsulfonyl carboxyl, or $C_{2-12}$ mono- or di-alkylcarbamoyl;

$R_3$ and $R_4$, independent from each other, are $C_{1-6}$ alkyl;

either $R_5$ is hydrogen, hydroxyl, $C_{2-6}$ alkanoyloxy, $C_{7-12}$ aroyloxy, carbamoyloxy, formyloxy, $C_{2-6}$ alkoxycarbonyloxy, $C_2$-$C_{12}$ mono- or di-alkylcarbamoyloxy, and $R_6$ is hydrogen, or $R_5$ and $R_6$ together are a bond;

$R_7$ and $R_8$, independent from each other, are selected from the following: $C_{1-6}$ perfluoroalkoxy, $C_{1-6}$ perfluoroalkyl, $C_{1-6}$ alkyl, $C_{1-6}$ alkoxy, hydroxyl, $C_{2-6}$ alkoxycarbonyl, nitro, cyano, halogeno, $C_{1-6}$ alkylsulfonamido, $C_{1-6}$ perfluoroalkylsulfonamido, amino, $C_{1-6}$ alkanoylamino, $C_{2-6}$ perfluoroalkanoylamino, $C_{1-12}$ mono- or di-alkylamino, $C_{1-6}$ alkylsulfonyl, $C_{6-12}$ arylsulfonyl, carboxyl, $C_{2-12}$ mono- or di-alkylcarbamoyl, or hydrogen;

and $R_9$ is hydrogen, $C_{1-6}$ alkyl, $C_{2-6}$ alkylcarbonyl or $C_{1-6}$ alkylsulfonyl;

or a pharmaceutically acceptable salt thereof.

The most preferred compounds are represented by formula (I) wherein:

$R_1$ is trifluoromethoxy, methoxy, nitro, cyano, chloro, bromo, fluoro, trifluoromethyl, methanesulfonamido, $C_{1-3}$ alkyl, $C_{1-6}$ mono or dialkylamino, acetamido, trifluoroacetamido or trifluoromethanesulfonamido;

$R_2$ is hydrogen, trifluoromethoxy, methoxy, nitro, cyano, chloro, bromo, fluoro, trifluoromethyl, methanesulfonamido, $C_{1-3}$ alkyl, $C_{1-6}$ mono or dialkylamino, acetamido, trifluoroacetamido or trifluoromethanesulfonamido;

$R_3$ and $R_4$ are methyl;

either $R_5$ is hydrogen or hydroxyl, and $R_6$ is hydrogen, or $R_5$ and $R_6$ together form a bond;

$R_7$ and $R_8$, independent from each other, are hydrogen, trifluoromethoxy, methoxy, nitro, cyano, chloro, bromo, fluoro, methyl, trifluoromethyl, methanesulfonamido, $C_{1-3}$ alkyl, $C_{1-6}$ mono or dialkylamino, acetamido, trifluoroacetamido, or trifluoromethanesulfonamido;

and $R_9$ is hydrogen or methyl;

or a pharmaceutically acceptable salt thereof.

It is understood that the definition of the compounds of formula (I), when $R_5$ is hydrogen or hydroxy and $R_6$ is hydrogen encompass all possible stereoisomers and mixtures thereof. In particular, it encompasses racemic modifications and any optical isomers. Optical isomers may be obtained in pure form by standard separation techniques. The pharmaceutically acceptable salts of these compounds are prepared by reaction of the free compound of formula (I) with organic or inorganic acids or bases. The pharmaceutically acceptable salts are those derived from such organic and inorganic acids as: acetic, lactic, citric, tartaric, succinic, maleic, malonic, hydrochloric, hydrobromic, phosphoric, nitric, sulfuric, methanesulfonic, and similarly known acceptable acids. Where $R_1$ and/or $R_2$ are carboxyl groups, or $R_9$ is a proton, salts of the compounds of this invention may be formed with bases such as the alkali metals (Na, K, or Li) or the alkaline earth metals (Ca or Mg).

The present invention also provides a process for the preparation of a compound of formula (I). More particularly, the compounds of formula (I) wherein $R_5$ is hydroxy and $R_6$ is hydrogen may be prepared by one of the following processes:

a) reacting a compound of formula (II)

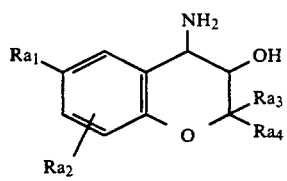

wherein $Ra_1$, $Ra_2$, $Ra_3$, $Ra_4$ are $R_1$, $R_2$, $R_3$, $R_4$, respectively, as defined hereinbefore or a group or atom convertible thereto, with a compound of formula (III).

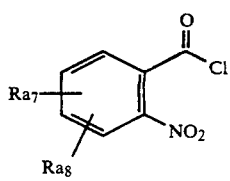

wherein $Ra_7$ and $Ra_8$ are $R_7$ and $R_8$ as defined hereinbefore or a group or atom convertible thereto in a solvent such as dichloromethane, in the presence of an acid scavenger such as triethylamine to give a compound of formula (IV).

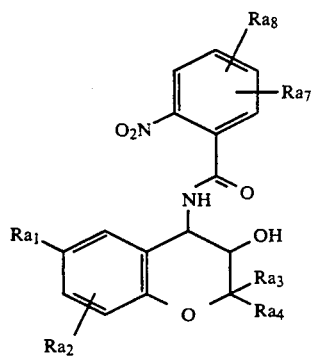

This intermediate is then allowed to react under reducing conditions so as to facilitate the formation of the desired bonds, for example by warming in methanolic water at alkaline pH in the presence of zinc metal to give compounds of formula (I) with $R_5$=hydroxy and $R_6$=H.

b) reacting a compound of formula (V).

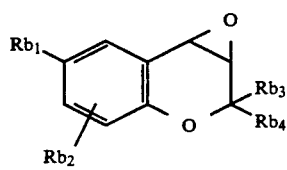

wherein $Rb_1$, $Rb_2$, $Rb_3$, and $Rb_4$ are $R_1$, $R_2$, $R_3$, and $R_4$, respectively, as defined hereinbefore or a group or atom convertible thereto, with a compound of formula (VI).

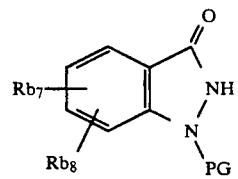

wherein $Rb_7$ and $Rb_8$ are $R_7$ and $R_8$, respectively, as defined hereinbefore or a group or atom convertible thereto, PG is a suitably removable and compatible nitrogen protecting group. It is particularly preferred that the reaction between the compounds of formula (V) and (VI) is conducted under basic conditions so as to facilitate the formation of the anion of (VI), for example, in the presence of sodium hydride. Examples of hydrolytic removal of the protecting group (PG) are generally known in the art of organic synthesis to give a compound of formula (I) with $R_5$=hydroxy and $R_6$=H.

Using either process, the compound of formula (I) wherein $R_5$ is hydroxy and $R_6$ is hydrogen may be optionally dehydrated according to methods known in the art of organic synthesis to give a compound of formula (I) wherein $R_5$ and $R_6$ together are a bond. The compound of formula (I) wherein $R_5$ is hydroxy and $R_6$ is hydrogen may be optionally de-oxygenated according to methods known in the art of organic synthesis to give a compound of formula (I) wherein $R_5$ and $R_6$ are both hydrogen.

As mentioned previously, the compounds of formula (I) have been found to relax smooth muscles and have blood pressure lowering activity. They are therefore useful in the treatment of hypertension. Furthermore, the compounds of formula (I) are active as potassium channel activators which render them useful for treatment of peripheral vascular disease, congestive heart failure, stroke, anxiety, cerebral anoxia and other neurodegenerative disorders, disorders involving excessive smooth muscle contraction of the urinary tract (such as incontinence), or of the gastro-intestinal tract (such as irritable bowel syndrome), asthma, and hair loss.

The compounds of this invention are distinguished from prior art by their unique pharmacological profile. In addition to a more favorable shorter duration of action in the standard experimental, spontaneous hypertensive rat (SHR) model, these compounds show evidence of greatly diminished reflex tachycardia, as well as desireable effects on neuronal tissue which renders them useful for treatment of neurodegenerative disorders.

The present invention accordingly provides a pharmaceutical composition which comprises a compound of this invention and a pharmaceutically acceptable carrier. In particular, the present invention provides an anti-hypertensive pharmaceutical composition which comprises an antihypertensive effective amount of a compound of this invention and a pharmaceutically acceptable carrier.

The compositions are preferably adapted for oral administration. However, they may be adapted for other modes of administration, for example parenteral administration for patients suffering from heart failure and in the form of an aerosol for intrabronchial administration to asthmatics.

In order to obtain consistency of administration, it is preferred that a composition of the invention is in the form of a unit dose. Suitable unit dose forms include tablets, capsules and powders in sachets or vials. Such unit dose forms may contain from 0.1 to 100 mg of a compound of the invention and preferably from 2 to 50 mg. Still further preferred unit dosage forms contain 5 to 25 mg of a compound of the present invention. The compounds of the present invention can be administered orally at a dose range of about 0.01 to 100 mg/kg or preferably at a dose range of 0.1 to 10 mg/kg. Such compositions may be administered from 1 to 6 times a day, more usually from 1 to 4 times a day.

The compositions of the invention may be formed with conventional excipients, such as a filler, a disintegrating agent, a binder, a lubricant, a flavoring agent and the like. They are formulated in conventional manner, for example, in a manner similar to that used for known antihypertensive agents, diuretics and $\beta$-blocking agents.

The present invention further provides a compound of the invention for use as an active therapeutic substance. Compounds of formula (I) are of particular use in the treatment of hypertension and/or smooth muscle relaxation.

The present invention further provides a method of treating hypertension in mammals including man, which comprises administering to the afflicted mammal an antihypertensive effective amount of a compound or a pharmaceutical composition of the invention.

The following examples are presented to illustrate rather than limit the methods for production of representative compounds of the invention.

EXAMPLE 1

(−)-2-[(3S,4R)-3-Hydroxy-2,2-dimethyl-6-trifluoromethoxy-chroman-4-yl]-1,2-dihydro-indazol-3-one

Step 1) Preparation of N-[(3S,4R)-3-Hydroxy-2,2-dimethyl-6-(trifluoromethoxy)-chroman-4-yl]-2-nitrobenzamide (3S,4R)-4-Amino-2,2-dimethyl-6-(trifluoromethoxy)-chroman-3-ol [prepared by the method of Quagliato et al. *Biorg. & Med. Chem. Let.* 1991 1, 39; (2.75 g, 10 mmol)] and triethylamine (1.39 mL, 10 mmol) were stirred together in dichloromethane (25 mL) at 0° C. To this solution was added a solution of 2-nitrobenzoyl-chloride (1.32 mL, 10 mmol) in dichloromethane (10 mL). The ice bath was allowed to gradually warm to 15° C. overnight. The crude benzamide was diluted with dichloromethane (50 mL), washed with water (2×10 mL), dried (MgSO4) and concentrated to afford 2.0 g (47%) of white solid: m.p. 189°–190° C.; $^1$H NMR (DMSO-d$_6$): δ 9.17 (d, 1H), 8.04 (d, 1H), 7.81 (m, 2H), 7.71 (t, 1H), 7.33 (s, 1H), 7.16 (d, 1H), 6.86 (d, 1H), 5.86 (d, 1H), 4.96 (br t, 1H), 3.64 (dd, 1H), 1.42 (s, 3H), 1.19 (s, 3H).

Step 2) Preparation of (−)-2-[(3S,4R)-3-Hydroxy-2,2-dimethyl-6-(trifluoromethoxy)-chroman-4-yl]-1,2-dihydro-indazol-3-one The above amide (2.0 g, 4.7 mmol) in methanol (10 mL) was added a solution of sodium hydroxide (0.8 g, 19 mmol) in water (15 mL). Zinc powder (300 mesh, 0.93 g, 14.3 mmol) was added and the resultant mixture was then heated to 70° C. for 24 hours. Zinc was removed by vacuum filtration of the cooled mixture. Some methanol was removed in the process. The filtrate was titrated to neutral pH with dilute HCl and then extracted with dichloromethane. The organic phase was dried (Na$_2$SO$_4$), concentrated and the residue was purified by column chromatography (1:1 hexanes/ethyl acetate) to afford a foam which was crystallized (hexane/diethylether/dichloromethane) to give 0.50 g (28%) of a white solid: mp 105° C.(shrink); $^1$H NMR (DMSO-d$_6$): δ 10.10 (s, 1H), 7.73 (d, 1H), 7.52 (t, 1H), 7.18 (d, 2H), 7.13 (t, 1H), 6.94 (d, 1H), 6.57 (s, 1H), 5.77 (d, 1H), 5.40 (br d, 1H), 4.12 (dd, 1H), 1.08 (s, 3H), 1.07 (s, 3H). IR (KBr): 3600–3200, 1630 cm$^{-1}$; MS (m/z) 395 (MH+); $[\alpha]_D^{25}$ = −85.88 (THF).

Elemental analysis for C$_{19}$H$_{17}$F$_3$N$_2$O$_4$: Calc'd: C, 57.87; H, 4.35; N, 7.10. Found: C, 57.88; H, 4.61; N, 6.77.

EXAMPLE 2

(−)-2-[(3S,4R)-3-Hydroxy-2,2-dimethyl-6-trifluoromethoxy-chroman-4-yl]-1-methyl-1,2-dihydro-indazol-3-one Iodomethane (0.062 mL, 1.0 mmol) was added to a stirring suspension of the product of Example 1 (0.39 g, 1.0 mmol) and potassium carbonate (0.13 g, 1.0 mmol) in dimethylformamide (2 mL) and the resulting mixture was stirred at ambient temperature overnight. Solvent was removed in vacuo, and the residual material was partitioned between ethyl acetate and water. The organic phase was dried (Na$_2$SO$_4$), concentrated and chromatographed (1:1 hexanes/ethyl acetate) to afford a foam that was ground and triturated with hexanes to yield 0.25 g (60%) of a white solid: mp 143°–144° C.; $^1$H NMR (CDCl$_3$): δ 7.75 (d, 1H), 7.56 (t, 1H), 7.07–7.14 (m, 4H), 6.88 (d, 1H), 5.72 (d, 1H), 4.18 (d, 1H), 3.05–3.16 (m, 2H), 2.81 (br s, 3H), 1.56 (s, 3H), 1.34 (s, 3H); IR (KBr): 3500–3200, 1645 cm$^{-1}$. MS (m/z) 408 (M+).

Elemental analysis for C$_{20}$H$_{19}$F$_3$N$_2$O$_4$: Calc'd: C, 58.82; H, 4.69; N, 6.86. Found: C, 58.70; H, 4.64; N, 6.84.

EXAMPLE 3

(−)-2-[(3S,4R)-3-Hydroxy-2,2-dimethyl-6-trifluoromethoxy-chroman-4-yl]-6-chloro-1,2-dihydro-indazol-3-one

Step 1) Preparation of N-[(3S,4R)-3-Hydroxy-2,2-dimethyl-6-(trifluoromethoxy)-chroman-4-yl]-4-chloro-2-nitrobenzamide 4-Chloro-2-nitrobenzoic acid (2.02 g, 10 mmol) was converted to the corresponding acid chloride by refluxing in benzene (30 mL) with thionyl chloride (2.38 g, 20 mmol) for 2 hours. The crude mixture was concentrated in vacuo and diluted with dichloromethane (10 mL). This solution was added to a cooled solution of (3S,4R)-4-amino-2,2-dimethyl-6-(trifluoromethoxy)-chroman-3-ol (2.75 g, 10 mmol), triethylamine (1.39 mL, 10 mmol) and dichloromethane (25 mL). The crude benzamide was worked-up in a method similar to that in Example 1 and chromatographed (1:1 hexanes/ethyl acetate) to afford 2.0 g (43%) of white solid: m.p. 64°–66° C.; $^1$H NMR (DMSO-d$_6$): δ9.24 (d, 1H), 8.19 (s, 1H), 7.96 (d, 1H), 7.83 (d, 1H), 7.29 (s, 1H), 7.18 (d, 1H), 6.86 (d, 1H), 5.88 (d, 1H), 4.94 (br t, 1H), 3.64 (dd, 1H), 1.42 (s, 3H), 1.19 (s, 3H).

Step 2) Preparation of (−)-2-[(3S,4R)-3-Hydroxy-2,2-dimethyl-6-(trifluoromethoxy)-chroman-4-yl]-6-chloro-1,2-dihydro-indazol-3-one To the above amide (1.8 g, 4.0 mmol) in methanol (10 mL) was added a solution of sodium hydroxide (0.65 g, 16 mmol) in water (15 mL). Zinc powder (300 mesh, 0.80 g, 12.2 mmol) was added to the resultant mixture which was then heated overnight and worked-up as in Example 1 to afford a foam which was ground and triturated with hexanes to give 0.50 g (29%) of a white powder: mp 236°–238° C.; $^1$H NMR (DMSO-d$_6$): δ10.48 (s, 1H), 7.74 (d, 1H), 7.26 (s, 1H), 7.20 (s, 1H), 7.13 (d, 1H), 6.95 (d, 1H), 6.59 (s, 1H), 5.80 (d, 1H), 5.40 (br d, 1H), 4.08–4.12 (m, 1H), 1.45 (s, 3H), 1.24 (s, 3H). IR (KBr): 3500–3200, 1630 cm$^{-1}$; MS (m/z) 429 (MH$^+$); $[\alpha]_D^{25} = -76.72$.

Elemental analysis for C$_{19}$H$_{16}$ClF$_3$N$_2$O$_4$: Calc'd: C, 53.22; H, 3.76; N, 6.53. Found: C, 52.90; H, 3.93; N, 7.18.

EXAMPLE 4

(−)-2-[(3S,4R)-3-Hydroxy-2,2-dimethyl-6-trifluoromethoxy-chroman-4-yl]-6-trifluoromethyl-1,2-dihydro-indazol-3-one

Step 1) Preparation of N-[(3S,4R)-3-Hydroxy-2,2-dimethyl-6-(trifluoromethoxy)-chroman-4-yl]-4-trifluoromethyl-2-nitrobenzamide 2-Nitro-α,α,α-trifluoro-p-toluic acid (2.02 g, 10 mmol) was converted to the corresponding acid chloride by refluxing in benzene (30 mL) with thionyl chloride (3.57 g, 30 mmol) for 2 hours. The crude mixture was concentrated in vacuo and diluted with dichloromethane (10 mL). This solution was added to a cooled solution of (3S,4R)-4-amino-2,2-dimethyl-6-(trifluoromethoxy)-chroman-3-ol (2.75 g, 10 mmol), triethylamine (1.39 mL, 10 mmol) and dichloromethane (25 mL). The crude benzamide was worked-up in a method similar to that in Example 1 and chromatographed (2:1 hexanes/ethyl acetate) to afford 2.1 g (42%) of white solid: m.p. 60°–65° C.; $^1$H NMR (DMSO-d$_6$): δ9.34 (d, 1H), 8.44 (s, 1H), 8.30 (d, 1H), 8.04 (d, 1H), 7.32 (s, 1H), 7.18 (d, 1H), 5.93 (d, 1H), 5.93 (d, 1H), 4.97 (br t, 1H), 3.64 (dd, 1H), 1.43 (s, 3H), 1.20 (s, 3H).

Step 2) Preparation of (−)-2-[(3S,4R)-3-Hydroxy-2,2-dimethyl-6-(trifluoromethoxy)-chroman-4-yl]-6-trifluoromethyl-1,2-dihydro-indazol-3-one To the above amide (2.1 g, 4.25 mmol) in methanol (10 mL) was added a solution of sodium hydroxide (0.65 g, 16 mmol) in water (15 mL). Zinc powder (300 mesh, 0.80 g, 12.2 mmol) was added to the resultant mixture which was then heated overnight and worked-up as in Example 1 to afford a foam which was ground and triturated with hexanes to give 0.525 g (27%) of a white powder: mp 210°–212° C.; $^1$H NMR (DMSO-d$_6$): δ 10.76 (s, 1H), 7.96 (d, 1H), 7.52 (s, 1H), 7.40 (d, 1H), 7.20 (d, 1H), 6.96 (d, 1H), 6.65 (s, 1H), 5.83 (d, 1H), 5.46 (br d, 1H), 4.11–4.15 (m, 1H), 1.46 (s, 3H), 1.24 (s, 3H). IR (KBr): 3500–3200, 1650 cm$^{-1}$; MS (m/z) 463 (MH$^+$); $[\alpha]_D^{25} = -32.80$.

Elemental analysis for C$_{20}$H$_{16}$F$_6$N$_2$O$_4$: Calc'd: C, 51.96; H, 3.49; N, 6.06. Found: C, 52.02; H, 3.57; N, 5.95.

EXAMPLE 5

(−)-2-[(3S,4R)-3-Hydroxy-2,2-dimethyl-6-trifluoromethoxy-chroman-4-yl]-4-methyl-1,2-dihydro-indazol-3-one

Step 1) Preparation of N-[(3S,4R)-3-Hydroxy-2,2-dimethyl-6-(trifluoromethoxy)-chroman-4-yl]-6-methyl-2-nitrobenzamide 2-Methyl-6-nitrobenzoic acid (1.81 g, 10 mmol) was converted to the corresponding acid chloride by refluxing in benzene (30 mL) with thionyl chloride (1.66 g, 14 mmol) for 0.5 hours. The crude mixture was concentrated in vacuo and diluted with dichloromethane (10 mL). This solution was added to a cooled solution of (3S,4R)-4-amino-2,2-dimethyl-6-(trifluoromethoxy)-chroman-3-ol (2.75 g, 10 mmol), triethylamine (1.39 mL, 10 mmol) and dichloromethane (25 mL). The crude benzamide was worked-up in a method similar to that in Example 1 and chromatographed (1:1 hexanes/ethyl acetate) to afford 2.5 g (62%) of a white solid: m.p. 204°–206° C.; $^1$H NMR (CDCl$_3$): δ 8.02 (d, 1H), 7.58 (d, 1H), 7.48 (t, 1H), 7.20 (s, 1H), 7.04 (d, 1H), 6.82 (d, 1H), 6.06 (d, 1H), 3.80 (t, 1H), 3.70 (br s, 1H), 2.56 (s, 3H), 1.52 (s, 3H), 1.31 (s, 3H).

Step 2) Preparation of (−)-2-[(3S,4R)-3-Hydroxy-2,2-dimethyl-6-(trifluoromethoxy)-chroman-4-yl]-4-methyl-1,2-dihydro-indazol-3-one To the above amide (1.8 g, 4.0 mmol) in methanol (10 mL) was added a solution of sodium hydroxide (0.65 g, 16 mmol) in water (15 mL). Zinc powder (300 mesh, 0.80 g, 12.2 mmol) was added to the resultant mixture which was then heated overnight and worked-up as in Example 1 to afford a foam which was ground and triturated with hexanes/diethylether to give 0.171 g (9%) of a white powder: mp 104°–106° C.; $^1$H NMR (DMSO-d$_6$): δ 9.95 (s, 1H), 7.35 (t, 1H), 7.18 (d, 1H), 6.95 (d, 1H), 6.94 (d, 2H), 6.85 (d, 1H), 6.60 (s, 1H), 5.73 (d, 1H), 5.37 (br d, 1H), 4.08–4.13 (m, 1H), 2.65 (s, 3H), 1.45 (s, 3H), 1.23 (s, 3H). IR (KBr): 3500–3200, 1640 cm$^{-1}$; MS (m/z) 409 (MH$^+$); $[\alpha]_D^{25} = -68.40$ (THF).

Elemental analysis for C$_{20}$H$_{19}$F$_3$N$_2$O$_4$: Calc'd: C, 58.82; H, 4.69; N, 6.86. Found: C, 58.47; H, 4.85; N, 6.56.

EXAMPLE 6

(−)-2-[(3S,4R)-3-Hydroxy-2,2-dimethyl-6-trifluoromethoxy-chroman-4-yl]-5,6-dimethoxy-1,2-dihydro-indazol-3-one

Step 1) Preparation of N-[(3S,4R)-3-Hydroxy-2,2-dimethyl-6-(trifluoromethoxy)-chroman-4-yl]-4,5-dimethoxy-2-nitrobenzamide Methyl 4,5-dimethoxy-2-nitrobenzoate (4.8 g, 20 mmol) was hydrolyzed to the corresponding carboxylic acid by refluxing overnight with KOH (1.6 g, 40 mmol) in 1:1 methanol/benzene (100 mL). The mixture was concentrated to give the crude carboxylate, dissolved in H$_2$O, and precipitated as 4,5-dimethoxy-2-nitrobenzoic acid with 2N HCl. This acid (2.27 g, 10 mmol) was then converted to the corresponding acid chloride by refluxing in benzene (30 mL) with thionyl chloride (1.66 g, 14 mmol) for 1 hour. The crude mixture was concentrated in vacuo and diluted with dichloromethane (10 mL). This solution was added to a cooled solution of (3S,4R)-4amino-2,2-dimethyl-6-(trifluoromethoxy)-chroman-3-ol (2.75 g, 10 mmol), triethylamine (1.39 mL, 10 mmol)

and dichloromethane (25 mL). The crude benzamide was worked-up in a method similar to that in Example 1 and chromatographed (1:1 hexanes/ethyl acetate) to afford 2.74 g (56%) of white solid: m.p. 97°–100° C.; $^1$H NMR (DMSO-d$_6$): δ 9.00 (s, 1H), 7.62 (s, 1H), 7.39 (d, 1H), 7.25 (s, 1H), 7.16 (d, 1H), 6.86 (d, 1H), 5.86 (d, 1H), 4.96 (br t, 1H), 3,91 (s, 3H), 3.89 (s, 3H), 3.64 (dd, 1H), 1.43 (s, 3H), 1.20 (s, 3H).

Step 2) Preparation of (−)-2-[(3S,4R)-3-Hydroxy-2,2-dimethyl-6-(trifluoromethoxy-chroman-4-yl]-5,6-dimethoxy-1,2-dihydro-indazol-3-one To the above amide (1.8 g, 4.0 mmol) in methanol (10 mL) was added a solution of sodium hydroxide (0.65 g, 16 mmol) in water (15 mL). Zinc powder 300 mesh, 0.80 g, 12.2 mmol) was added to the resultant mixture which was then heated overnight and worked-up as in Example 1, and chromatographed (9:1 ethyl acetate/hexanes) to afford a foam which was ground and crystallized from diethylether/hexanes to give 0.24 g (11%) of an off-white powder: mp 127°-128° C.; $^1$H NMR (DMSO-d$_6$) δ 9.62 (s, 1H), 7.16 (d, 1H), 7.13 (s, 1H), 6.92 (d, 1H), 6.67 (s, 1H), 6.54 (s, 2H), 5.70 (d, 1H), 5.32 (br d, 1H), 4.07–4.09 (m, 1H), 3.81 (s, 3H), 3.80 (s, 3H), 1.45 (s, 3H) 1.23 (s, 3H). IR (KBr): 3600-3200, 1630 cm$^{-1}$; MS (m/z) 454 (M$^+$); $[\alpha]_D^{25} = -81.30$ (THF).

Elemental analysis for C$_{21}$H$_{21}$F$_3$N$_2$O$_6$: Calc'd: C, 55.51; H, 4.66; N, 6.16. Found: C, 55.11; H, 4.77; N, 6.19.

EXAMPLE 7

(+)-2-[(3R,4S)-3-Hydroxy-2,2-dimethyl-6-trifluoromethoxychroman-4-yl]-1,2-dihydro-indazol-3-one (+)-2-[(3R,4S)-3-Hydroxy-2,2-dimethyl-6-(trifluoromethoxy)-chroman-4-yl]-1,2-dihydro-indazol-3-one was prepared in two steps identical to those in Example 1 starting from (3R, 4S)-4-amino-2,2-dimethyl-6-(trifluoromethoxy)chroman-3-ol. Purification by column chromatography (9:1 dichloromethane/diethyl ether) afforded 0.20 g (11%) of a white solid: mp 105° C.(shrink); $^1$H NMR (DMSO-d$_6$): δ 10.10 (s, 1H), 7.73 (d, 1H), 7.52 (t, 1H), 7.18 (d, 2H), 7.13 (t, 1H), 6.94 (d, 1H), 6.57 (s, 1H), 5.77 (d, 1H), 5.40 (br d, 1H), 4.12 (dd, 1H), 1.08 (s, 3H), 1.07 (s, 3H). IR (KBr): 3600–3200, 1630 cm$^{-1}$; MS (m/z) 394 (M$^+$); $[\alpha]_D^{25} = +82.70$ (THF).

Elemental analysis for C$_{19}$H$_{17}$F$_3$N$_2$O$_4$: Calc'd: C, 57.87; H, 4.35; N, 7.10. Found: C, 57.57; H, 4.55; N, 6.62.

EXAMPLE 8

(−)-2-[(3S,4R)-3-Hydroxy-2,2-dimethyl-6-trifluoromethoxy-chroman-4-yl]-5-methyl-1,2-dihydro-indazol-3-one

Step 1) Preparation of N-[(3S,4R)-3-Hydroxy-2,2-dimethyl-6-(trifluoromethoxy)-chroman-4-yl]-5-methyl-2-nitrobenzamide 5-Methyl-2-nitrobenzoic acid (1.81 g, 10 mmol) was converted to the corresponding acid chloride by refluxing in benzene (30 mL) with thionyl chloride (1.66 g, 14 mmol) for 0.5 hours. The crude mixture was concentrated in vacuo and diluted with dichloromethane (10 mL). This solution was added to a cooled solution of (3S, 4R)-4-amino-2,2-dimethyl-6-(trifluoromethoxy)-chroman-3-ol (2.75 g, 10 mmol), triethylamine (1.39 mL, 10 mmol) and dichloromethane (25 mL). The crude benzamide was worked-up in a method similar to that in Example 1 to afford 3.37 g (82%) of a white solid: m.p. 185°–187° C., $^1$H NMR (DMSO-d$_6$): δ 9.12 (d, 1H), 7.96 (d, 1H), 7.60 (s, 1H), 7.51 (d, 1H, 7.38 (s, 1H), 7.16 (d, 1H), 6.86 (d, 1H), 5.84 (d, 1H), 5.00 (t, 1H), 3.66 (m, 1H), 2.45 (s, 3H), 1.43 (s, 3H), 1.20 (s, 3H).

Step 2) Preparation of (−)-2-[(3S,4R)-3-Hydroxy-2,2-dimethyl-6-(trifluoromethoxy)-chroman-4-yl]-5-methyl-1,2-dihydro-indazol-3-one To the above amide (3.37 g, 7.65 mmol) in ethanol (40 mL) was added a solution of sodium hydroxide (1.40 g, 35.0 mmol) in ethanol (40 mL). Zinc powder (300 mesh, 1.63 g, 24.9 mmol) was added to the resultant mixture which was then heated overnight and worked-up as in Example 1 but chromatographed (1:9 diethylether/dichloromethane) to afford 0.554 g (18%) of a white powder: mp 110°–112° C.; $^1$H NMR (DMSO-d$_6$): δ 9.83 (s, 1H), 7.52 (s, 1H), 7.35 (d, 1H), 7.17 (d, 1H), 7.09 (d, 1H), 6.93 (d, 1H), 6.54 (s, 1H), 5.74 (d, 1H), 5.38 (br d, 1H), 4.08–4.12 (m, 1H), 2.37 (s, 3H), 1.45 (s, 3H), 1.23 (s, 3H), JR (KBr): 3500–3200, 1630 cm$^{-1}$; MS (m/z) 409 (MH$^+$); $[\alpha]_D^{25} = -78.22$ (THF).

Elemental analysis for C$_{20}$H$_{19}$F$_3$N$_2$O$_4$ (¼ H$_2$O): Calc'd: C, 58.18; H, 4.76; N, 6.78. Found: C, 58.06; H, 4.72; N, 6.48.

The blood pressure lowering activity of the compounds of this invention was established in accordance with standard pharmaceutically accepted test procedures in representative compounds as follows:

Male Okamoto-Aoki spontaneously hypertensive rats (SHR) ranging in weight from 250–400 g were anesthetized with halothane. Their left femoral arteries and veins were cannulated with polyethylene tubing of the appropriate size (i.d. 0.023", o.d. 0.038"). Each animal was placed in a Bollman cage, and the tail, along with two cannulas, was extended through a hole in one end of the cage. The tail was taped securely to a firm rubber board to prevent the rat from turning in its cage to dislodge the cannulas. The femoral arterial cannula was connected to a Statham pressure transducer which in turn was attached to a polygraph for recording arterial pressure and pulse rate. The pulse rate was considered to be the heart rate.

After the blood pressure has stabilized (usually 2 hours after cessation of the anesthesia), standard agonists were injected by the i.v. route. The doses administered were: isoproterenol 0.5 μg/kg, adrenaline 2.0 μg/kg, tyramine 200 μg/kg and angiotensin-I 0.25 μg/kg. The agonists were given in random order except that tyramine was never preceded by isoproterenol as the response to tyramine seemed to be blunted after a prior injection of isoproterenol. Enough time was allowed for the BP to return to preinjection levels before the test compound was administered by gastric lavage. The time of drug administration was designated as time zero. Heart rate and blood pressure were recorded at 5,10,15,30,45 and 60 minutes and hourly thereafter for a period of 4 hours after drug administration. At 1 and 2 hours post-drug the agonists were again injected at the same concentration and in the same order as during the control period.

For each dose, the maximum fall in blood pressure was given in mm Hg and also expressed as a percentage decrease compared to pretreatment control values. Linear regression on the maximum decrease in mean arterial blood pressure at each dose was used to calculate the ED$_{30}$ (the dose which would lower mean arterial pressure by 30%). A decrease in mean arterial blood pressure of 30% reduces the blood pressure from the hypertensive to the normotensive range. The results of oral administration of various doses of representative compounds of this invention are given in Table I.

TABLE I

Blood Pressure Lowering by Compounds of Formula (I)

| Example | mg/kg. (p.o.) | n | Pre-treat MABP mm Hg | Max Δ BP mm Hg minutes and hours | | Pre-treat HR beats/min | Max Δ HR beats minutes and hours | |
|---|---|---|---|---|---|---|---|---|
| 1 | 1.0 | 3 | 190 ± 15 | −112 (45 m) −92 (4 h) | −59 ± 4 −47 ± 15 | 389 ± 28 | +41 (45 m) −31 (4 h) | +11 ± 12 −9 ± 13 |
|   | 0.3 | 6 | 186 ± 4 | −102 (30 m) −22 (4 h) | −55 ± 2 −12 ± 4 | 389 ± 21 | +90 (30 m) +36 (4 h) | +25 ± 6 +10 ± 4 |
|   | 0.1 | 7 | 190 ± 7 | −41 (15 m) −13 (2 h) | −21 ± 3 −7 ± 2 | 398 ± 22 | +58 (15 m) −29 (2 h) | +16 ± 6 −7 ± 3 |
| 2 | 1.0 | 4 | 181 ± 8 | −22 (45 m) | −13 ± 2 | 469 ± 4 | +17 (45 m) | +4 ± 1 |
| 7 | 1.0 | 3 | 188 ± 9 | −96 (30 m) −20 (4 h) | −51 ± 1 −11 ± 2 | 386 ± 23 | +114 (30 m) +38 (4 hr) | +31 ± 7 +10 ± 4 |
|   | 0.1 | 4 | 184 ± 6 | −12 (5 m) | −7 ± 1 | 399 ± 16 | +39 (5 m) | +10 ± 3 |

In addition, smooth muscle relaxing activity of the compounds of this invention was established in accordance with standard pharmaceutically accepted test procedures in representative compounds as follows:

Sprague-Dawley rats (150–200 g) are rendered unconscious by $CO_2$ asphyxiation and then euthanized by cervical dislocation. The bladder is removed into warm (37 deg.C.) physiological salt solution (PSS) of the following composition (mM): NaCl, 118.4; KCl, 4.7; $CaCl_2$, 2.5; $MgSO_4$, 4.7; $H_2O$, 1.2; $NaHCO_3$, 24.9; $KH_2PO_4$, 1.2; glucose, 11.1; EDTA, 0.023; gassed with 95% $O_2$; 2/5% $CO_2$; pH 7.4. The bladder is opened and then cut into strips 1–2 mm in width and 7–10 mm in length. The strips are subsequently suspended in a 10 ml tissue bath under an initial resting tension of 1.5 g. The strips are held in place by two surgical clips one of which is attached to fixed hook while the other is attached to an isometric force transducer. The preparations, which usually exhibit small spontaneous contractions, are allowed to recover for a period of 1 hour prior to a challenge with 0.1 uM carbachol. The carbachol is then washed out and the tissue allowed to relax to its resting level of activity. Following 1 further 30 min period of recovery an additional 15 mM KCl are introduced into the tissue bath. This increase in KCl concentration results in a large increase in the amplitude of spontaneous contractions (and initiation of contractions in previously quiescent strips) superimposed upon a small increase in basal tone. Following stabilization of this enhanced level of contractile activity, incremental increases in the concentration of test compound or vehicle are introduced into the tissue bath. Contractile activity is measured for each compound or vehicle concentration during the last min of a 30 min challenge.

Isometric force developed by the bladder strips is measured using a concentration required to elicit 50% inhibition of pre-drug contractile activity ($IC_{50}$ concentration) is calculated from this concentration-response curve. The maximum percentage inhibition of contractile activity evoked by a test compound is also recorded for concentrations of test compound < or equal to 30 uM.

TABLE II

Inhibition of Contractions in Isolated Rat Bladder Strips

| Compound | n | $IC_{50}$ | Inhibition of Force (%) at (x) μM |
|---|---|---|---|
| Example 1 | 3 | 44 nM | 100 (0.3) |
| Example 2 | 3 | 9 μM | 58 (10) |
| Example 8 | 2 | 11 nM | |

Hence, the compounds of this invention have a pronounced effect on smooth muscle contractility and are useful in the treatment of hypertension, urinary incontinence, irritable bladder and bowel disease, asthma, stroke and similar disease states as mentioned above, which are amenable to treatment with potassium channel activating compounds by administration, orally, parenterally, or by aspiration to a patient in need thereof.

Applicable solid carriers for the compounds of this invention include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection or as aerosols for inhalation therapy. Sterile solutions can also be intravenously. Oral administration may be in either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific situation must be subjectively determined by the attending physician. The variables involved include the specific disease state, route of administration and the size, age and response pattern of the patient.

What is claimed is:
1. The compound which is (−)-2-[(3S,4R)-3-hydroxy-2,2-dimethyl-6-trifluoromethoxy-chroman-4-yl]-5-methyl-1,2-dihydro-indazol-3-one, or a pharmaceutically acceptable salt thereof.

* * * * *